United States Patent
Smith et al.

(10) Patent No.: US 6,670,128 B2
(45) Date of Patent: Dec. 30, 2003

(54) TRANSFUSION MEDICINE LEUKODEPLETION FILTER DEVICES AS A SOURCE OF GENETIC MATERIAL FOR GENOTYPING STUDIES

(75) Inventors: Martin A. Smith, Brookline, MA (US); Galina N. Fomovskaia, Boston, MA (US); Mikhail A. Fomovsky, Boston, MA (US); Neil J. Butt, Cambridge (GB); Matthew Baker, Ely (GB)

(73) Assignee: Whatman, Inc., Newton, MA (US)

( * ) Notice: Subject to any disclaimer, the term of this patent is extended or adjusted under 35 U.S.C. 154(b) by 0 days.

(21) Appl. No.: 09/930,429

(22) Filed: Aug. 15, 2001

(65) Prior Publication Data

US 2002/0090623 A1 Jul. 11, 2002

Related U.S. Application Data

(60) Provisional application No. 60/225,854, filed on Aug. 16, 2000.

(51) Int. Cl.[7] .............. C12Q 1/68; C12P 19/34; C12M 1/34; C07H 21/02; C07H 21/04
(52) U.S. Cl. .............. 435/6; 435/7.1; 435/91.1; 435/91.2; 435/287.2; 536/22.1; 536/23.1; 536/24.3; 536/24.31; 536/27.32; 536/27.33; 210/767; 422/50; 436/518
(58) Field of Search .............. 435/6, 7.1, 91.1, 435/91.2, 287.2; 536/22.1, 23.1, 24.3, 24.31–24.33; 210/767; 422/50

(56) References Cited

U.S. PATENT DOCUMENTS

| | | | |
|---|---|---|---|
| 4,666,828 A | 5/1987 | Gusella | 435/6 |
| 4,683,202 A | 7/1987 | Mullis | 435/91 |
| 4,801,531 A | 1/1989 | Frossard | 435/6 |
| 5,192,659 A | 3/1993 | Simons | 435/6 |
| 5,272,057 A | 12/1993 | Smulson et al. | 435/6 |
| 5,498,520 A | 3/1996 | Chapman | |
| 5,658,548 A | 8/1997 | Padhye et al. | 423/335 |
| 5,663,045 A | 9/1997 | Chapman | |
| 6,103,192 A * | 8/2000 | Stapleton et al. | 422/50 |
| 6,337,026 B1 * | 1/2002 | Lee et al. | 210/767 |

OTHER PUBLICATIONS

Duff et al., Research Advances in Alzheimer's Disease and Related Disorders, Pathogenic Mutation Insertion Into YAC, "Insertion of a Pathogenic Mutation into a Yeast Artificial Chromosome Containing the Human APP Gene and Expression ES Cells", pp. 722–745, J. Wiley & Sons (1995).

K.T. Arndt et al., "Preparation of Clone Libraries in yeast Artificial–Chromosome Vectors", Methods in Enzymology, 194:251–270.

Mario R. Capecchi, "Altering the Genome by Homologous Recombination" Science, 244:1288–1292 (1991).

James M. Cregg et al., "Recent Advances in the Expression of Foreign Genes in *Pichia pastoris*", Bio/Technology, 11:905–909 (1993).

Nicholas P. Davies et al., "Targeted alterations in yeast artificial chromosomes for inter–species gene transfer", Nucleic Acids Research, 20(11):2693–2698 (1992).

Paul Dickinson et al., "High frequency gene targeting using insertional vectors", Human Molecular Genetics, 2(8):1299–1302 (1993).

Clare Huxley et al., "The Human HPRT Gene on a yeast Artificial Chromosome is Functional When transferred to Mouse Cells by Cell Fusion", Genomics, 9:742–750 (1991).

Aya Jakobovits et al., "Germ–line transmission and expression of a human–derived yeast artificial chromosome", Nature, 362:255–258 (1993.

Bruce T. Lamb et al., "Introduction and expression of the 400 kilobas precursos amyloid protein gene in transgenic mice", Nature Genetics 5:22–30 (1993).

Barbara E. Pearson et al., "Expression of the human β–amyloid precursor protein gene from a yeast artificial chromosome in transgenic mice", Proc. Natl. Acad. Sci. USA, 90:10578–10582 (1993).

Rodney Rothstein, Targetign, disruption, Replacement, and Allete Rescue: Integrative DNA Transformation in Yeast, Methods in Enzymology, 194:281–301 (1991).

Andreas Schedl et al., "A yeast artificial chromosome covering the tyrosinase gene confers copy number–dependent expression in transgeni mice", Nature, 362:258–361 (1993).

William M. Strauss et al., "Germ Line Transmission of a Yeast Artificial Chromosome Spanning the Murine $\alpha_1(I)$ Collagen Locus", Science, 259:1904–1907 (1993).

Eli Gilboa et al., "Transfer and Expression of Cloned Genes Using Retroviral Vectors", Bio Techniques, 4(6):504–512 (1986).

* cited by examiner

Primary Examiner—Jeffrey Siew
(74) Attorney, Agent, or Firm—Edwards & Angell, LLP

(57) ABSTRACT

The present invention provide methods for utilizing spent leukodepletion filter devices as a source of material for the isolation and analysis of genomic DNA (gDNA), including polymorphism, genotyping, and pharmacogenomic studies. Cellular retentate with the filter contains leukocytes, which are lysed to release the nuclei. The nuclei are lysed or ruptured to release genomic DNA, which is then isolated and used for subsequent analysis.

34 Claims, 1 Drawing Sheet

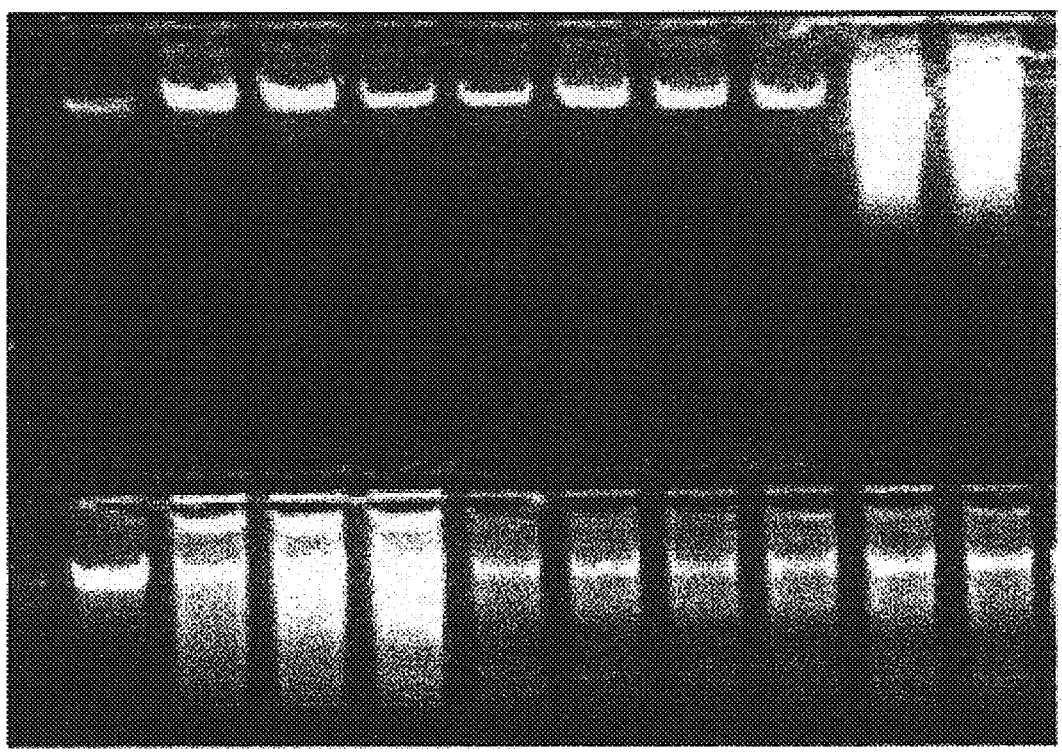

TRANSFUSION MEDICINE LEUKODEPLETION FILTER DEVICES AS A SOURCE OF GENETIC MATERIAL FOR GENOTYPING STUDIES

CROSSREFERENCE TO RELATED APPLICATIONS

This claims priority of U.S. Provisional Patent Application 60/225,854, filed Aug. 16, 2000, which is incorporated herein by reference.

FIELD OF THE INVENTION

The present invention relates to methods for isolating leukocytes and genetic materials therefrom. It also relates, in part, to a method for isolating genetic material, such as genomic DNA, from spent leukodepletion or leukoreduction filter devices in order to analyze the genetic material.

BACKGROUND OF THE INVENTION

Each year in the United States about 14 million transfusions of blood or blood components take place. There are three major blood products in transfusion medicine:
1. RED BLOOD CELLS (RBC, typically about 340 ml contained in 1 unit of donor blood)—the remaining red cell mass after most of the plasma is removed.
2. PLATELETS (typically 300 ml/1 unit of donor blood) or platelet concentrates (PCs, typically further concentrated to about 50 ml/1 unit of donor blood)—one platelet concentrate (one unit of random donor platelets) is derived from one unit of donor blood.
3. FRESH FROZEN PLASMA (FFP, 225 ml/1 unit of donor blood)—One unit of FFP can raise coagulation factor levels by 8% and fibrinogen by 13 mg/dl in the average patient.

Despite the increasing need for transfusions and the use of transfusion products, such use involves a number of risks. About 150,000 patients each year experience adverse reactions to such products. Such adverse reactions occur regardless of the type of blood transfusion a patient receives. Ninety percent of adverse transfusion reactions are caused by donor leukocytes contained in the transfusion products.

Further problems stem from Human Leukocyte Antigen (HLA) alloimmunization, in which the recipient is sensitized to antibodies contained in the transfusion product which can react, for example, to the recipient's leukocytes (HLA sensitization).

Where the recipient suffers from a non-hemolytic febrile transfusion reaction, the patient most frequently experiences fever, chills, and nausea due to white blood components contained in the transfusion product, to which the patients has antibodies (usually anti-HLA).

Other serious risks of the use of transfusion products include transmission and/or reactivation of cytomegalovirus (CMV), occurrence of graft-versus-host disease (GVHD), and the risk of viral transmissions. (HIV, HCV transmission are the most feared complications of transfusion.)

Certain precautions have been adopted in order to reduce the likelihood and/or severity of adverse reactions to transfusion products. Leukoreduction of blood products before transfusion into a patient is considered the most significant recent improvement in safety and purity of blood transfusion. Leukoreduction is the process of removing >99.9% of the white blood cells (WBC) from cellular blood components (red cells and platelets).

Leukodepletion (LD) (also known as leukoreduction) is a technique most commonly carried out by the filtration of whole blood or blood products to remove nucleated cells (leukocytes) from a donated sample required for transfusion. LD is a very potent measure employed by the transfusion medicine industry to avoid the risk of transferring disease from donor to patient and also as a prevention of adverse immuno-response to the donated blood.

The FDA has announced publicly that it will require that all cellular blood components transfused in the U.S be leukoreduced (leukodepleted) by the year 2002. Worldwide, ten countries, including Canada, Britain, France, Portugal, and Germany, have mandated universal leukocyte reduction, and 13 more, including Denmark, Italy, Japan, and New Zealand, are moving toward the practice.

As in any essential step of blood processing, the step of leukoreduction is subject to quality control. In order to label a component as leukocyte-reduced (leukoreduced), the American Association of Blood Bank Standards (19th ed) requires that the residual leukocyte content in the component must be $<5\times10^6$ WBC/unit blood. European guidelines define leukocyte reduction as residual leukocyte content of $<1\times10^6$ leukocytes/unit.

FDA guidelines state that quality control testing of leukocyte-reduced units should be performed on at least 1% of products (or 4/month for facilities preparing <400 units/month) and that 100% of tested units are required to contain $<5\times10^6$ residual leukocytes/unit.

Most LD techniques employ a filter system that specifically captures leukocytes from blood, allowing the other desired blood components to pass. Specific leukocyte capture by filtration can either be carried out by affinity interaction of a leukocyte cell surface antigen such as P-selectin, CD44 or CD8, for example, or more commonly by a physical entrapment of the relatively larger leukocytes within the filter matrix of an LD device. In either case, an LD filter device, once used for the removal of leukocytes from a donated blood unit (600 ml), contains a very high concentration of leukocytes.

Potentially, assuming 100% leukodepletion, the spent LD filter device will contain between $36\times10^8$ and $6\times10^9$ cells. Each leukocyte is nucleated; i.e., it contains a nucleus that is the storage organelle for genomic DNA (gDNA), the molecular representation of an organism's genetic makeup. Therefore, a spent LD filter device containing many leukocytes will also carry the genetic makeup of the donor.

Genotyping is the discipline of identifying an individual's genome in relation to disease-specific alleles and/or mutations that occur as an effect of parental linkage. The rapid purification of human genomic DNA is an essential part of a genotyping process; the genomic DNA of an individual being the structural unit for the entire DNA sequence of every allele expressed.

Human genomic DNA cannot be directly sequenced. In order to carry out sequence analysis on regions of the chromosomes that may contain portions of mutation or disease specific sequences, selected portions are amplified, e.g., via polymerase chain reaction ("PCR"), and the amplified products are sequenced. The selected portions of the chromosomes that are amplified are dictated by the specific sequence of the primers used in the PCR amplification. The primer sets that are used in genotyping studies are commercially available and are representative for the chromosome under examination. If linkage studies identify that a disease-bearing sequence is on a particular chromosome, then many primer sets will be utilized across that chromosome in order to obtain genetic material for sequencing. The resultant PCR products may well represent the entire chromosome under examination. Due to the large length of chromosomes, many PCR reactions are carried out on the genomic DNA template from a single patient.

Human genomic DNA is currently purified by a variety of methods (Molecular Cloning, Sambrook et al. (1989)). Consequently, many commercial kit manufacturers provide products for such techniques, for example: AmpReady™ (Promega, Madison, Wis.), DNeasy™ (Qiagen, Valencia, Calif.), and Split Second™ (Roche Molecular Biochemicals, Indianapolis, Ind.). These products rely on the use of specialized matrices or buffer systems for the rapid isolation of the genomic DNA molecule.

Recently, microporous filter-based techniques have surfaced as tools for the purification of genomic DNA as well as a whole multitude of nucleic acids. The advantage of filter-based matrices are that they can be fashioned into many formats that include tubes, spin tubes, sheets, and microwell plates. Microporous filter membranes as purification support matrices have other advantages within the art. They provide a compact, easy to manipulate system allowing for the capture of the desired molecule and the removal of unwanted components in a fluid phase at higher throughput and faster processing times than possible with column chromatography. This is due to the fast diffusion rates possible on filter membranes. Nucleic acid molecules have been captured on filter membranes, generally either through simple adsorption or through a chemical reaction between complementary reactive groups present on the filter membrane or on a filter-bound ligand resulting in the formation of a covalent bond between the ligand and the desired nucleic acid.

Porous filter membrane materials used for non-covalent nucleic acid immobilization have included materials such as nylon, nitrocellulose, hydrophobic polyvinylidinefluoride (PVDF), and glass microfiber. A number of methods and reagents have also been developed to also allow the direct coupling of nucleic acids onto solid supports, such as oligonucleotides and primers (e.g. J. M. Coull et al., Tetrahedron Lett. vol. 27, page 3991; B. A. Conolly, Nucleic Acids Res., vol. 15, page 3131, 1987; B. A. Conolly and P. Rider, Nucleic Acids Res., vol. 12, page 4485, 1985; Yang et al., P.N.A.S. vol. 95: 5462–5467). UV cross-linking of DNA (Church et al., PNAS, vol. 81, page 1991, 1984), The Generation Capture Column Kit (Gentra Systems, Minneapolis, Minn.) and RNA (Khandjian et al., Anal. Biochem, vol. 159, pages 227, 1986) to nylon membranes have also been reported.

More recently, glass microfiber, has been shown to specifically bind nucleic acids from a variety of nucleic acid containing sources very effectively (See, e.g., M. Itoh et al., *Simple and Rapid Preparation of Plasmid Template by a Filtration Method using Microtiter Filter Plates*, 25 Nucl. Acids Res., 1315, 1315–1316 (1997); B. Andersson et al., *Method for 96-well M13 DNA Template Preparations for Large-Scale Sequencing*, 20 BioTechniques 1022, 1022–1027 (1996)). Under the correct salt and buffering conditions, nucleic acids will bind to glass or silica with high specificity.

Commercially available leukodepletion filters are often made of glass fibers, polyester fibers, or a combination of the two types of fibers. One such commercially available leukodepletion filter, the r\LS leukodepletion filter media (HemaSure, Inc.), for example, combines a matrix of fibers, such as glass fibers, with components, such as a highly fibrillated fibers or particles comprising a polyacrylonitrile copolymer having a specific surface area greater than 100 $m^2/g$ and an average diameter of less than 0.05 μm, and, optionally, a binder, such as a polyvinyl alcohol or its derivative. This filter is capable of removing at least 99.99% of the leukocytes from a unit of blood product to provide a leukodepleted blood product. Other commercial leukodepletion filters are available from manufacturers, such as the Pall Purecell LRF High Efficiency Leukocyte Reduction Filtration System (Pall Corporation) and leukoreduction products by Baxter Healthcare Corporation (Fenwal Division)/Asahi Medical Corporation.

As the medical industry becomes more prognostic in nature, and drug companies strive to understand the genetic variations within a population set, which causes different reactions to a given drug compound, the need to study the genetic makeup of that population is essential. In order to carry out such population genetics studies (polymorphism studies), gDNA must be obtained from all the contributors of the study.

For example, New York Blood Center ("NYBC") is the world's largest blood bank currently collaborating with organizations, such as Academic Medicine Development Company ("AMDeC")/North Shore University (New York, N.Y.), to carry out polymorphism studies (300,000 people per study). Currently NYBC sells units of whole blood to AMDeC for extraction of gDNA from the units. Typically, the first step of gDNA extraction from blood is to isolate cells which contain genomic DNA; this is almost always carried out by centrifugation. Centrifugation, although well established, is very time consuming and inefficient in terms of yield, and DNA shearing may also occur during centrifugation steps. The cells in whole blood which contain genomic DNA are, at least primarily, leukocytes.

Extraction of gDNA from whole blood units is both time-consuming and expensive. Moreover, the use of blood units for gDNA extraction competes with patient treatment for the already inadequate supply of whole blood at a time of increasing demand.

SUMMARY OF THE INVENTION

The present invention provides methods which utilize spent leukodepletion filter devices as a source of material for isolation and analysis of genomic DNA, including analyses for polymorphism, genotyping, and pharmacogenomic studies, as well as procedures to efficiently remove high quality intact gDNA molecules from leukodepletion filters.

According to the present invention, a method is provided for utilizing spent leukodepletion filter devices as a source for the isolation of genomic DNA for analysis.

According to the present invention, a method is provided for utilizing spent leukodepletion filter devices, comprising filters with leukocytes retained as a cellular retentate, as a source for the isolation of genomic DNA for analysis, the method comprising:

(a) providing a leukodepletion filter device having cellular retentate containing leukocytes;

(b) lysing the cellular retentate to form a cell lysate;

(c) treating the filter to remove cell lysate from the filter while retaining leukocyte nuclei with the filter;

(d) rupturing the leukocyte nuclei retained with the filter in step (c) and removing the non-nucleic acid contents of the nuclei from the filter while retaining the contents of the nuclei including nucleic acids; and (e) eluting the nucleic acid.

In one embodiment, an LD filter device is treated with solutions which are DNase-free. The leukocytes retained with the filter (cellular retentate) are then lysed with a cell lysis agent to form a cell lysate, which is removed from the filter, while the leukocyte nuclei and contents of the nuclei, including genomic DNA, are retained by the filter. The leukocyte nuclei retained with the filter are then ruptured, preferably with a nucleus lysis agent. At least a substantial amount of nucleic acid, including genomic DNA, is retained by the filter, while the debris from the ruptured nuclei is removed. Elution of the nucleic acid is then performed, preferably using heat and a DNA liberating medium, preferably either sterile, DNase-free water or an appropriate elution buffer.

In one embodiment, the elution buffer (or water) is heated to an elevated temperature prior to addition to the filter. In another embodiment, unheated elution buffer (or water) is added to the filter, followed by heating of the filter together with the elution buffer (or water). In a preferred embodiment, the elution buffer (or water) is heated to an elevated temperature prior to addition to the filter, followed by incubation of the filter and elution buffer (or water) together at an elevated temperature that may be the same as, or different than, the elevated temperature used for the initial heating of the buffer or water.

The present invention further provides for DNA analysis kits, comprising the materials used to liberate DNA from cells retained on a leukocyte depletion filter. Preferably, the kits also comprise reagents which are used for the desired DNA analysis. For example, a preferred kit comprises a cell lysis agent, which preferably lyses cellular membranes without lysing at least a substantial portion of nuclear membranes, a nucleus lysing medium, which lyses the membrane of nuclei, a DNA liberating medium, and a set of primers for carrying out analysis of at least one target portion of the genomic DNA. The kit may include other components useful to the analysis, e.g., further purifying agents, filters or columns, reagents for carrying on DNA amplification and/or analysis, and analytical materials and/or devices for recognizing the presence of DNA sequences which are the subject of the analysis.

In a preferred embodiment, contaminating red blood cells retained with the filter are lysed and removed, such as with a red cell lysis buffer, prior to the lysis of the leukocytes retained with the filter.

It is preferred that the leukocyte nuclei be ruptured after removal of the cell lysate contaminants.

In a preferred embodiment, a method is provided for utilizing spent leukodepletion filter devices, comprising filters with leukocytes retained as a cellular retentate, as a source for the isolation of genomic DNA for analysis, the method comprising:

(a) providing a leukodepletion filter device having cellular retentate including leukocytes;
(b) lysing the cellular retentate to form a cell lysate;
(c) treating the filter to remove the cell lysate from the filter, while retaining leukocyte nuclei on the filter;
(d) rupturing the leukocyte nuclei retained with the filter in step (c) and removing the non-nucleic acid contents of the nuclei from the filter while retaining the contents of the nuclei including nucleic acids;
(e) heating an elution buffer to an elevated temperature of 40° C. to 125° C.;
(f) adding the elution buffer to the filter;
(g) heating the filter and elution buffer to an elevated temperature of 4°° C. to 125° C.; and
(h) eluting the nucleic acid.

While the present method focuses on removal of the DNA of interest, which is removable by heat and elution, other methods of freeing the DNA from the filter material are also contemplated. For example, where the bonds between the molecules of interest and the filter are more chemical or immunological in nature, chemical agents which break the bonds, or antigens which supplant the bound material in the immunological bond can be used.

The present invention will now be described in further detail with reference to the accompanying Examples and to the attached Figures in which:

BRIEF DESCRIPTION OF THE DRAWINGS

FIG. 1 is a photograph of a DNA electrophoresis depicting certain materials described more fully below.

DETAILED DESCRIPTION OF THE INVENTION

Large blood centers carry out many hundreds of leukodepletions each week. The spent LD filter devices filled with genomic DNA-containing leukocytes could, therefore, serve as a source of material required by the investigators of the polymorphism of interest. In effect, institutes carrying out polymorphism studies could purchase spent LD filter devices and extract the gDNA from them. This also allows genotypers to access genetic material without drawing their own blood samples or those of donors.

For example, as described above, NYBC, the world's largest blood bank, currently sells units of whole blood to organizations, such as AMDeC, to extract the gDNA from the units in order to carry out polymorphism studies (300,000 people per study). Typically, the first step of gDNA extraction from blood is to isolate leukocytes, generally by centrifugation, which is is very time consuming and inefficient in terms of yield.

The present invention provides the ability to use spent LD filter devices, and through a simple, non-centrifugal, methodology, extract massive amounts of donor gDNA. Not only is the gDNA obtained at low cost, but NYBC has the potential to recover the cost of the LD procedure, which is required for every unit of blood that is donated. The system of the invention supplants the present approach of purchasing and purifying units of whole blood. Not only is that system monetarily expensive, but it also competes with patient treatment for our precious and inadequate supply of whole blood. Furthermore, with such a simple system for providing gDNA, genotyping institutes can easily obtain the specific demographic populations their studies require, for example, the sub-group of LD filter devices from a particular ethnic group, from males vs. females, or for example, from male smokers over age forty. Ideally, patient demographics and other information are recorded without compromising patient confidentiality.

Upon receipt of a spent LD filter device containing intact leukocytes from the blood donor, the genotyping institute simply removes the gDNA in the simple manner described in Examples 1 and 2. It must be noted that a spent LD filter device, usually a cartridge, has standardized tubing attached to it. This tubing arrangement is readily hooked to pump systems. Blood is presented to the LD cartridge and filtrate collected via the tube and pump system. Therefore, using the same tube and pump system, buffers, waste products, and eluate, all of which are required for gDNA extraction from the entrapped leukocytes, can be presented. Many LD filter devices rely on glass microfiber filter matrices to physically entrap leukocytes from presented blood.

This invention proposes a simple methodology for the extraction of gDNA from such glass filters found within a spent LD filter device. The method is fast, requiring only a few buffers and a simple heat elution step to recover the DNA. The method does not rely on chaotrophic salt, ion exchange, or affinity extraction procedures.

More generally, this invention proposes the use of spent LD filter devices as a ready source of gDNA for the isolation and analysis of genomic DNA.

Traditionally, filters are selected so as to have a pore size and composition which will act as a barrier so as to prevent the material to be filtered from passing through or into the filter material. For example, by selecting a filter material with a particular pore size it is possible to prevent materials with a particle size greater than the pore size from passing through or into the filter material. For example, where the sample comprises a blood product, the filter may be chosen having a pore size such that the RBC, platelets, and plasma pass through the filter, while the white cells containing the nucleic acid are retained by the filter as a retentate. Red cell lysis is often not necessary as the filter will allow most intact red cells to pass through. However, prior to isolation of nucleic acids from the spent leukodepletion filter device, treatment with a red blood cell lysis solution may lead to a cleaner final product.

Alternatively, however, the retentate may interact chemically with the filter. It is possible that a combination of adsorption and absorption may take place.

The present method provides a quick, simplified, cost effective method for using leukodepletion filter devices bearing leukocytes, devices ordinarily consigned to medical waste disposal, as a source of genomic DNA isolation that is not manually intensive or technique-dependent and does not utilize hazardous chemicals. The nucleic acid produced in accordance with the present invention is capable of multiple downstream processing.

The present invention provides a method for utilizing spent leukodepletion filter devices, comprising filters with leukocytes retained as a cellular retentate, as a source for the isolation of genomic DNA for analysis, the method comprising:
  (a) providing a leukodepletion filter device bearing leukocytes having nuclei which contain genomic DNA;
  (b) lysing the cellular retentate to form a cell lysate while retaining leukocyte nuclei in the filter, the leukocyte nuclei containing genomic DNA;
  (c) removing the cell lysate from the filter and retaining the leukocyte nuclei;
  (d) rupturing the leukocyte nuclei retained with the filter in step (c) and removing contaminants while retaining the nucleic acid; and
  (e) eluting the nucleic acid.

A "spent" leukodepletion filter device is one that has been used for blood collection. Alternatively, any leukodepletion filter bearing leukocytes may be used. A spent leukodepletion filter device is preferred for its availability, for increased recovery of genomic DNA, and for providing a means of re-using material which would otherwise be consigned to medical waste.

It is preferred that the retentate be lysed while entrapped within the filter. However, it should be understood that the method according to the present invention encompasses also an embodiment where substantially all or some of retentate is lysed while retained by, but not entrapped within, the filter, including on the surface of the filter.

In one aspect of the invention, the leukocyte membrane is ruptured or gently "peeled away" to release the leukocyte nucleus, which is retained by the filter.

In another aspect of the present invention, the cell retentate comprises intact whole cells as well as, or instead of, cell debris. Advantageously, the intact whole cells may be treated in step (b), while being retained by the filter, by the application of a detergent to the filter. Any detergent may be used, provided that it has the effect of rupturing or "peeling away" the cell membrane to leave condensed nuclear material. The condensed nuclear material is retained by the filter. Preferably the detergent is selected from sodium dodecyl sulfate ("SDS") or other commercially available detergents such as TWEEN™ 20, lauryl dodecyl sulfate ("LDS"), 3-[(3-cholamidopropyl)dimethylammonio]-1-propanesulfonate ("CHAPS"), or TRITON™ X-100. The amount of detergent employed is sufficient to lyse cell membranes, but not so much as to denature DNA and preferably not so much as to rupture the nuclei. More preferably the detergent is selected from the group of 0.5% weight-by-volume (w/v) SDS, 1% volume-by-volume (v/v) TWEEN™ 20, 1% w/v LDS, or 1% v/v TRITON™ X-100. Suitable amounts are generally 0.01% to 2% by weight (w/v) and preferably 0.01% to 1.0% w/v and more preferably 0.05% to 0.5% w/v. Most preferably the detergent is 0.5% w/v SDS.

While the addition of detergent to the retentate is preferable, the present method may be carried out without the addition of a detergent by using other known lysing agents, such as low-salt non-isotonic solutions, such as ethanol or sucrose. However, applying a detergent to the retentate while the retentate is retained by the filter increases the yield and purity of the DNA product.

In addition to rupturing the intact whole cells, the detergent also has the function of washing out protein and haem which may have been retained by the filter.

With regard to lysis if the nuclei, in one aspect of the invention, the nuclei are lysed, exploded, or ruptured to form a lysate containing nucleic acid by the addition of a low-salt, non-isotonic buffer, such as a hypotonic buffer. Preferably, the low salt buffer is Solution 3: Per 1 liter—
  Measure 500 ml purified water
  Add 10.0 ml (9.9–1.1 ml) 1M Tris (Whatman WB420003)
  Add 0.596 g (0.595–0.597 g) KCl (Whatman WB410015)
  Add 0.29 g (0.28–0.30 g) $MgCl_2$ (Whatman WB410014)
  Mix to dissolve
  Add 10.0 ml NFB (alternatively, fetal calf serum may be used) and mix
  Add 0.5 g (0.49–0.51 g) Na-Metabisulfite (Whatman WB410055) and mix
  Add water to 1000 ml and mix well.
  Aseptically filter solution through an 0.2 $\mu$m filter in a class II safety cabinet
  Store at room temperature ("Solution 3," as described in Example 2), 10 mM Tris-HCl; 1 mM EDTA; pH 7.6–8 ("AE," as described in Example 1), 10 mM Tris-HCl; 0.1 mM EDTA; pH 8 ("TE$^{-1}$"), or water. Other suitable lysis solutions include any detergent-containing solutions in which the detergent may be cationic, anionic or neutral. Chaotrope-containing solutions, preferably buffers may also be used. The lysis solution lyses or bursts open the condensed nuclear material to release the nucleic acid. It will be understood by the skilled person, however, that lysing the nuclei to form a lysate containing nucleic acid also can be achieved by other methods, for example, by heating.

Lysis, whether of cells or of nuclei, and the removal of the contaminating materials resulting from lysis may take place sequentially, such as lysis of cells followed by removal of non-nucleic materials or contents or lysis of nuclei followed by removal of non-nucleic acids. Alternatively, the lysis and removal steps may occur simultaneously or may overlap.

The retention or entrapment of the cells and nucleic acid by the filter may arise by virtue of a physical or size-related barrier relating to the dimensions of the filter material including the pore size and depth of the filter, or by other means. Without wishing to be bound by theory, it is thought that the nucleic acid may be physically associated with the filter rather than chemically or otherwise tightly bound thereto. It is postulated that nucleic acid-nucleic acid interactions themselves are important in maintaining a sufficiently high cross-sectional area to retard movement of the nucleic acid through the filter. Alternatively, however, chemical interactions may influence retention.

Filter materials that are suitable for use in the present invention include any material which enables the cells to be retained by the filter as a retentate and the nucleic acid to be retained by the filter, preferably in the form of a web.

Suitable materials include glass fiber or any silica-based or derived filters and plastic-based filters, for example, polyester and polypropylene based filters. Commercially available filters have been described in the Background of the Invention. One such commercially available leukodepletion filter, the r\LS leukodepletion filter media (HemaSure, Inc.), for example, combines a matrix of fibers, such as glass fibers, with components, such as highly fibrillated fibers or particles comprising a polyacrylonitrile copolymer having a specific surface area greater than 100 $m^2$/g and an average diameter of less than 0.05 $\mu$m, and, optionally, a binder, such as a polyvinyl alcohol or its derivative. Further description of these types of filters is found in U.S. Pat. No. 6,337,026 (U.S. Ser. No. 09/264,276, filed Mar. 8, 1999), which is incorporated herein by reference.

Certain filter materials, including glass microfiber, woven or non-woven polyethylene, woven or non-woven polyester, or woven or non-woven polypropylene, make it possible to isolate nucleic acid in the absence of a chaotrope. These are fibrous microfiber matrices that entangle or entrap nucleic acids released upon lysis of the nucleus. It is thought that without a fibrous matrix, entrapment levels may be low.

It is preferred also that the filter composition and dimensions are selected so that the nucleic acid in step (e) is capable of being eluted at a pH of from pH 5 to 11 or preferably from pH 5.8 to 10. This is advantageous in the present method because elution of the product nucleic acid in a more highly alkaline medium potentially can degrade the product. Accordingly, one preferred pH for elution is from 7 to 9.

"Nucleic materials" and "materials from the nucleus" include the nuclear envelope and the contents of the nucleus, including genomic DNA ("gDNA"). The "non-nucleic acid contents of the nucleus" include the components of the nuclear envelope and any other proteins or other substances of the nucleus that are not nucleic acids.

"Nucleic acids" include deoxyribonucleic acids (DNA) and ribonucleic acids (RNA) of various types. "Genetic material" comprises genomic DNA ("gDNA"), which is one type of DNA and encodes genetic information.

Any solution at any pH which is suitable for eluting the nucleic acid from the filter is acceptable. Preferred elution solutions include Na acetate (1 mM to 1M), 10 mM 2-[N-morpholino]-ethanesulfonic acid ("MES") (pH 5.6), 10 mM 3-[cyclohexylamino]-1-propanesulfonic acid ("CAPS") (pH 10.4), TE, $TE^{-1}$, SDS, TWEEN™ 20, LDS, or TRITON™ X-100. More preferred solutions include 0.5% SDS, 1% TWEEN™ 20, 1% LDS, or 1% TRITON™. Most preferred solutions include TE, $TE^{-1}$, AE, 10 mM Tris, and water. All yield approximately the same quantity of nucleic acid. Total yields of nucleic acid are higher when eluted in a high volume of elution solution.

Eluting the nucleic acid, in other words releasing the nucleic acid from the filter, may be affected in several ways. It is possible to elute nucleic acid from the filter at room temperature, but the efficiency of elution may be improved by putting energy into the system during an incubation step to release the nucleic acid prior to elution. This may be in the form of heat energy. Preferably, heat energy is put into the system by heating the nucleic acid to an elevated temperature for a predetermined time, while it is retained by the filter, prior to eluting in step (e), but not at a sufficiently high temperature or for such a time as to be damaged. More preferably, the nucleic acid is heated to an elevated temperature in the range of 40° C. to 125° C., even more preferably in the range of from 80° C. to 95° C. Most preferably, the nucleic acid is heated to an elevated temperature of about 90° C., advantageously for about 10 minutes.

Alternatively, elution buffer that has already been heated to an elevated temperature may be used in lieu of, or more preferably, in addition to, elution at an elevated temperature.

In a preferred embodiment, the elution step described above takes place as follows:

(a) heating an elution buffer to an elevated temperature of 40° C. to 125° C.;

(b) adding the elution buffer to the filter;

(c) heating the filter and elution buffer to an elevated temperature of 40° C. to 125° C.;

(d) eluting the nucleic acid; and (e) repeating steps (a)–(d) together at least once.

More preferably, the elevated temperature is in the range from 80° C. to 95° C.

Aside from the elution steps described above, the temperature for the non-elution steps is usually ambient temperature, typically in the range from 5° C. to 40° C.

While the method is applicable to any nucleic acid, it is preferred that that the nucleic acid comprises DNA, especially genomic DNA.

It is preferred that the method be conducted without any centrifugation steps.

It is preferred that the method be conducted substantially in the absence of a chaotrope.

This method is particularly useful for extraction of gDNA from a leukodepletion filter device. One suitable method for extracting gDNA involves the following steps:

i) A red blood cell-lysis solution is delivered to the filter in order to lyse any remaining contaminant red blood cells;

ii) The red blood cell-lysis solution is drawn through the filter leaving white blood cells with the filter;

iii) A white cell-lysis solution is delivered to the filter;

iv) The white cell-lysis solution is drawn through the filter leaving the leukocyte nuclei with the filter. Preferably the leukocyte nuclei remain intact for a cleaner product and better yield;

v) A low-salt, non-isotonic buffer is delivered to the filter to cause the leukocyte nuclei to rupture;

vi) The low-salt, non-isotonic buffer is drawn through the filter leaving the nucleic acid associated with the filter. It is apparent that ionic interaction is minimal, and accordingly, it appears that there is a physical association with the filter and a physical retarding of the movement of the nucleic acid through the filter.

vii) Further low salt buffer or water, preferably pre-heated to an elevated temperature, is delivered to the filter. This is then heated at a temperature and for a sufficient time to release the DNA from the filter. Preferably, the column is heated to a temperature within the range 80–95° C. for a time of approximately 10 minutes;

viii) The genomic DNA is eluted in the low salt buffer or water. The gDNA is of multiplex PCR quality.

While it is indicated in this preferred method that genomic DNA is the desired target compound, it is possible to use the method of the present invention to isolate RNA from an RNA-containing sample.

Typical red blood cell lysis solutions that may be used in the method of the invention include those set out in Table 1. A preferred solution is 0.83% w/v ammonium chloride; 0.16% w/v ammonium carbonate; 0.1 mM EDTA ("Solution 1," described in Example 2).

A kit according to a preferred embodiment of the present invention comprises:

(a) a cell lysis solution for cell lysis;

(b) a hypotonic solution for rupturing leukocyte nuclei;

(c) an elution buffer;

(d) means for removing the solutions, (e) at least one reagent suitable for analysis of liberated DNA.

Reagents suitable for analysis of liberated DNA can include any reagent suitable for PCR, processing of DNA, digesting or subcloning of DNA or portions thereof, sequencing of DNA, restriction fragment length polymorphism ("RFLP") analysis, Southern blotting and any other downstream applications generally found within the scope of DNA analysis. Reagents include, but are not limited to, probes, primers, restriction enzymes, buffers, proteins, indicators, and any other reagent useful for analysis of DNA.

TABLE 1

Solutions.

| Reference | Vol Blood | Vol Lysis Solution | Composition | Treatment |
|---|---|---|---|---|
| Millar et al (1988) N.A.R 16:1215 | | 3 ml | 10 mM Tris-HCL ph 8.2 400 mM NaCl 2 mM EDTA | Treat o/n Prot K |
| Nelson & Krawetz (1992) Anal Biochem 207:197–201 | 1 Vol | 5 Vol | 17 mM Tris-HCL pH 7.65 140 mM NH₄Cl | 37° C. for 5 min |
| Ramirez-Solis et al (1992) Anal Biochem 201:331–335 | 1 ml | 3 ml | 155 mM NH₄Cl 10 mM NaHCO₃ | 4° C. for 10–15 min |
| Douglas et al (1992) Anal Biochem 201:362–365 | 1 ml | 1 ml of 2x RBC lysis | 1x:- 11% sucrose 10 mM MgCl₂ 10 mM Tris-HCl pH 7.5 1% Triton X-100 | pellet and wash with 1x |
| Linblom and Holmlund (1988) Gene Anal Techn | 5 ml | 10 ml | 1% Triton X-100 320 mM sucrose 1 mM | pellet/ urea and phenol |
| 5:97–101 | 0.2–2 ml | 20 ml | Tris-HCl pH 7.5 5 mM MgCl₂ 20 mM Tris-HCl pH 8.0 5 mM EDTA | Used with Leukosorb type filler |
| Herrmann and Frischauf (1987) in Guide to Molecular Cloning p180–183 | 10 ml | 30 ml | 155 mM NH₄Cl 10 mM NH₄CO₃ 0.1 mM EDTA | ice 15 min, spin |

General Methods in Molecular Biology: Standard molecular biology techniques known in the art and not specifically described were generally followed as in Sambrook et al., *Molecular Cloning: A Laboratory Manual*, Cold Spring Harbor Laboratory Press, New York (1989); in Ausubel et al., *Current Protocols in Molecular Biology*, John Wiley and Sons, Baltimore, Md. (1989); in Perbal, *A Practical Guide to Molecular Cloning*, John Wiley & Sons, New York (1988); in Watson et al., *Recombinant DNA*, Scientific American Books, New York; in Birren et al. (eds), *Genome Analysis: A Laboratory Manual Series, Vols.* 1–4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al. 1996, Blood 87:3822.)

EXAMPLES

Example 1

General Method for Extraction of Genomic DNA (gDNA) from a Spent Leukodepletion Filter Device Upon receipt of a spent LD filter device that will contain intact leukocytes from the blood donor, the genotyping institute can simply remove gDNA in the following simple manner described below. It must be noted that a spent LD filter device, usually a cartridge, has standardized tubing attached to it. This tubing arrangement is readily hooked up to pump systems. Blood is presented to the LD cartridge and filtrate collected via the tube and pump system. Therefore using the same tube and pump system, buffers, waste product, and eluate, all of which are required for gDNA extraction from the entrapped leukocytes, can be presented.

The simple, non-centrifugal, non-ionic, non-chaotrophic and non-affinity extraction of gDNA from LD filter devices may be carried out as follows:

1. To the spent LD filter add 10 filter volumes of wash buffer (0.5% w/v SDS). The wash buffer removes any remaining red blood cells from the LD filter. The concentration of SDS used in this wash does not normally cause nuclei disruption, but will disrupt leukocyte cell membranes and removes non-nucleus cell debris.

2. After the wash buffer step, add 10 filter volumes of AE buffer (10 mM Tris-HCl; 1 mM EDTA; pH7.6–8) were applied. The AE buffer changes the isotonic composition of the filter surroundings and therefore, as a low-salt, hypotonic buffer, causes the entrapped leukocyte nuclei to explode or rupture. The explosion of nuclei within the LD filter causes a decompression of the packaged gDNA within them. As the gDNA decompresses, it entraps itself within the fibrous matrix of the LD filter. Preferably, this entrapment is not salt or pH specific—it is primarily physical.

3. After AE application to the LD filter, either 1 filter volume of elution buffer at RT is applied and the sample is heated for 10 minutes at 80° C., or 80° C. elution buffer is applied directly. Elution buffer is typically deonized water, TE, or AE. The physical incubation of heat is enough to dislodge the decompressed gDNA from the LD filter. Cold water, cold TE, or cold AE does not remove gDNA from the filter matrix.

4. After heat incubation, pump pressure is applied for collecting the gDNA-containing eluate.

Example 2

DNA Extraction From r\LS Filters after Their Use for Leukodepletion of RBC Units The goal was to evaluate various protocols based on the Whatman BioSciences Purification System (WBPS) for extracting gDNA from the matrices of r\LS filters (HemaSure, Inc.) that had previously been used for leukodepletion of RBC units. Protocols were evaluating the yield and quality of the collected DNA.

Materials:

Three r\LS filters were used, each of which had been used on the day of the experiment for filtration of an RBC unit. Filters were delivered on ice within three hours after filtration. The amount of DNA in each cartridge was predicted to be equal to 12–19 mg, taking into account the leukocyte concentration in the RBC unit prior to filtration.

Solutions (Whatman BioScience Genomic DNA Purification System): Solutions were prepared DNase-free as follows:

Solution 1:
0.83% Ammonium chloride
0.16% Ammonium carbonate
0.1 mM EDTA
Solution 2:
0.5% SDS
Solution 3:
Per 1 liter—
Measure 500 ml purified water
Add 10.0 ml (9.9–1.1 ml) 1M Tris (Whatman WB420003)
Add 0.596 g (0.595–0.597 g) KCl (Whatman WB410015)
Add 0.29 g (0.28–0.30 g) $MgCl_2$ (Whatman WB410014)
Mix to dissolve
Add 10.0 ml NFB (alternatively, fetal calf serum may be used) and mix
Add 0.5 g (0.49–0.51 g) Na-Metabisulfite (Whatman WB410055) and mix
Add water to 1000 ml and mix well.

Aseptically filter solution through an 0.2 $\mu$m filter in a Class II safety cabinet
Store at room temperature
Solution 4 (TE): TE, pH 8 (10 mM Tris; 1 mM EDTA) (alternatively, substitute water)

The resulting gDNA samples were examined for yield and quality of DNA. Quantitations of DNA were performed by spectrophotometry at $OD_{260}/OD_{280}$ and by spectrofluorometry with PicoGreen dye. The quality of each DNA sample was assessed following electrophoresis on an 0.8% agarose gel for 30 minutes at 90V.

Extraction Procedure:

Three different extraction protocols were evaluated:

1. Cartridge N13:
   Washed with Solution 1 (Red Cell Lysing Buffer) using a 60 ml syringe, two times (30–35 ml each time);
   Washed with Solution 2 (twice, 30–35 ml each time);
   Washed with 35 ml of Solution 3 (described above) (Whatman BioScience Genomic DNA Purification System);
   Filled the cartridge with 80°–85° C. DNase-free sterile water;
   Incubated the filled cartridge at 90° C. for 15 minutes;
   Attached the cartridge to the ISMATEC IPS pump and eluted DNA with sterile water at 90° C.;
   Collected the DNA solution into four tubes (13(1), 13(2), 13(3), and 13(4)), in volumes of 14 ml each.

2. Cartridge N12:
   Removed the residual RBC suspension from the cartridge with air by exerting pressure using a 60 ml syringe;
   Washed with Solution 1 using a 60 ml syringe, two times (30–35 ml each time); removed the Solution 1 by exerting pressure using a 60 ml syringe;
   Washed with Solution 2 (twice, 30–35 ml each time); removed the Solution 2 after each wash by exerting pressure using a 60 ml syringe;
   Washed with 35 ml of Solution 3; removed the Solution 3 by exerting pressure using a 60 ml syringe;
   Filled the cartridge with room temperature DNase-free sterile water;
   Incubated it at 90° C. for 30 minutes;
   Removed the DNA solution into a collection tube by exerting pressure with 60 ml syringe;.
   Repeated the two previous steps one additional time.
   Note that the DNA solution was collected into two tubes: 8 ml in 12(1) and 10 ml in 12(2).

3. Cartridge N9:
   Removed the residual RBC suspension from the cartridge with IX phosphate-buffered saline (PBS) buffer (10× PBS=137 mM NaCl; 2.7 mM KCl; 5.4 mM $Na_2HPO_4$; 1.8 mM $KH_2PO_4$; pH 7.4) by exerting pressure using a 60 ml syringe;
   Washed with Solution 1 using a 60 ml syringe, two times (30–35 ml each time); removed the Solution 1 by exerting pressure using a 60 ml syringe;
   Washed with Solution 2 (twice, 30–35 ml each time); removed the Solution 2 after each wash by exerting pressure using a 60 ml syringe;
   Washed with 35 ml of Solution 3; removed the Solution 3 by exerting pressure using a 60 ml syringe;
   Filled the cartridge with room temperature Solution 4 (TE buffer);
   Incubated it at 90° C. for 30 minutes;

Removed the DNA solution into a collection tube by exerting pressure with a 60 ml syringe;

Repeated the two previous steps one additional time.

Note that the DNA solution was collected into two tubes: 7 ml in 9(1) and 10 ml in 9(2).

Results:

DNA solutions extracted from the cartridges using different protocols were loaded onto a 0.8% agarose gel containing ethidium bromide (FIG. 1). The amount of collected DNA solution loaded in each lane was 5 µl. A solution of commercial human genomic DNA (Roche Molecular Biochemicals) was used as a control (Contr.). The amount of DNA in control samples loaded onto the gel was normalized to approximately 0.3 µg/well.

FIG. 1 is a photograph of the 0.8% agarose gel with the following samples (5 µl of collected DNA solution per lane):

Contr.—Control with commercial Human DNA

13(1)—DNA from cartridge N13, first 14 ml of the extraction solution

13(4)—DNA from cartridge N13, fourth 14 ml of the extraction solution

12(1)—DNA from cartridge N12, first extraction (8 ml of the extraction solution)

12(2)—DNA from cartridge N12, second extraction (17.5 ml of the extraction solution)

9(1)—DNA from cartridge N9, first extraction (7 ml of the extraction solution)

9(2)—DNA from cartridge N9, second extraction (10 ml of the extraction solution)

The quality of the DNA eluted from Cartridge N 13 was similar to the quality of control DNA (rows 13(1)-13(4) vs. Contr. Rows in FIG. 1). That is, there is no sign of DNA fragmentation, and the high molecular weight genomic DNA in the N 13 samples is apparently intact. In addition, the tight bands and lack of smearing indicate that the gDNA is double-stranded DNA ("dsDNA").

Electrophoresis images of the DNA samples extracted from Cartridge N9 and especially from Cartridge N12 demonstrate the existence of the ethidium bromide labeled fragments in wide range of molecular sizes, thereby indicating DNA fragmentation.

The results of the spectraphotometric and fluorometric (with PicoGreen dye) DNA measurements are represented in Table 2.

DNA measurements by both spectraphotometric and fluorometric methods of sample 13(1) were found to be similar. The optical density $OD_{260}/OD_{280}$ ratio of sample 13(4) (1.6657) was the closest to the $OD_{260}/OD_{280}$ ratio of the control sample (1.8251) and was not greater than 2.0. Also there was close agreement between DNA concentrations calculated for sample 13(4) based on $OD_{260}/OD_{280}$ and $OD_{260}/OD_{320}$ readings. Taken together with the gel electrophoresis results, these results indicate that the gDNA obtained using this protocol is of a quality useful for various downstream applications.

Based on optical density and fluorescence measurements the DNA concentrations in samples 13(1) and 13(4) were calculated to be in the range of 15–19 µg/ml. A total of ~1 mg DNA was collected from this cartridge. The recovery was calculated as ~7% of the amount of DNA predicted to be contained in the filter based on the leukocyte concentration of the RBC unit prior to leukodepletion (7 pg DNA/leukocyte), which, for this LD filter, corresponds to approximately 840 µg DNA.

The DNA solutions extracted from Cartridges N9 and N 12 were found to be lower in concentration in relation to the control DNA sample than were 13(1) and 13(4). The $OD_{260}/OD_{280}$ ratios measured for these samples were in the range of 1.17–1.33. The control DNA sample had an OD ratio equal to 1.83. Also, the DNA concentrations determined in these samples on basis of $OD_{260}/OD_{280}$, $OD_{260}/OD_{320}$ calculations or measured with PicoGreen fluorescence were found to be very different.

Conclusions:

In this study a good quality DNA was extracted from used r\LS filters only with the protocol used for Cartridge N13.

The DNA yield was ~1 mg/cartridge.

The recovery of DNA was found to be ~7% (approximately 840 µg), based on cell count of the RBC unit prior to leukodepletion.

Downstream Applications:

There are many downstream applications for genotyping and related analyses of the DNA isolated as described in this Example. A few of them are as follows:

1. PCR (single locus)
2. PCR (multi-locus/multiplex, STR profiling)
3. Real-time PCR
4. Restriction enzyme digestion (for cloning, restriction fragment length polymorphism ("RFLP"), Southern blotting)

With respect to PCR, probes or primers may be directed towards so-called "house-keeping regions" of genomic DNA, which include sequences of genomic DNA encoding proteins found in most types of cells in an organism, such as the genes encoding proteins involved in cell cycle, cell structure, or intracellular transport. One example is the gene encoding the cytoskeletal protein β-actin or a portion thereof. These sequences are typically used to evaluate the quality or amount of DNA recovered from a DNA isolation experiment. Alternatively, probes or primers may be specific for a disease, syndrome, polymorphism, or other sequence that is the particular focus of an experiment.

The amount of DNA isolated in this example (approximately 840 µg) is more than sufficient for many downstream applications, including those listed above. For example, a typical starting amount of template for PCR is in the region of 1 ng to 100 ng.

The three examples of PCR amplification listed above differ in terms of polymerase, primer design, cycle number, and quantification. Typically 1 ng gDNA is required for multiplex PCR, while larger amounts are required for single long PCR (particularly if the desired amplification region is >4 kb. Real-time PCR involves quantitating amounts of PCR products as they are amplified through the use of fluorescent markers on the primers and is particularly useful for amplifying low-copy or single-locus sequences. Real-time PCR typically requires 1–10 ng gDNA.

Once the concentration of the gDNA has been determined, usually via calculations from $OD_{260}$ measurements, the remaining PCR reaction components are added. Following amplification the products can be analyzed by a variety of methods that include gel electrophoresis, sequencing, fluorometric electropherogram, and chemiluminescence.

Restriction enzyme digestion requires (dsDNA as a template. Double-stranded DNA is incubated with one or more restriction enzymes in an appropriate buffer with any other required components at optimal temperature. For gDNA the reaction usually takes at least several hours and is performed with 500 ng template. Typical applications requiring restriction digestion include RFLP identification analysis, cloning and Southern blotting.

The restriction digestion reaction digests the gDNA template into fragments which can then be ligated into vectors, such as plasmid vectors (cloning experiments), resolved using gel electrophoresis (RFLP identification analysis), or resolved using gel electrophoresis followed by interrogation with gene-specific probes (Southern blotting for experiments concerning gene occurrence, chromosomal location, etc.).

Of course, other methods of downstream analysis may also be desirable.

TABLE 2

Spectrometric quantitation of DNA extracted from used r\LS filters (µg/ml).

| Samples | Sample Volume (ml) | $OD_{260}$ | $OD_{280}$ | $OD_{320}$ | $OD_{260}/OD_{280}$ | Conc. DNA (µg/ml) ($OD_{280}$) | Conc. DNA (µg/ml) ($OD_{320}$) | Conc. DNA (µg/ml) PicoGreen |
|---|---|---|---|---|---|---|---|---|
| N13(1) | 14 | 0.679 | 0.51 | 0.06 | 1.3322 | 16.67605 | 30.955 | 19 |
| N13(2) | 14 | 0.363 | 0.286 | 0.026 | 1.2691 | 7.57465 | 16.815 | |
| N13(3) | 14 | 0.193 | 0.148 | 0.013 | 1.3011 | 4.3931 | 9.01 | |
| N13(4) | 14 | 0.398 | 0.239 | 0.025 | 1.6657 | 15.67135 | 18.655 | |
| N12(1) | 8 | 3.416 | 2.902 | 0.413 | 1.1771 | 50.61915 | 150.14 | |
| N12(2) | 17.5 | 3.356 | 2.716 | 0.459 | 1.2356 | 63.0203 | 144.81 | 18 |
| N9(1) | 7 | 2.716 | 2.047 | 0.245 | 1.327 | 65.9359 | 123.585 | |
| N9(2) | 10 | 2.899 | 2.382 | 0.321 | 1.2171 | 50.9442 | 128.935 | 12 |
| Contr. DNA 3.3 µg/ml | | 0.074 | 0.041 | 0.004 | 1.8251 | 3.29975 | 3.485 | — |

Obviously, many modifications and variations of the present invention are possible in light of the above teachings. It is, therefore, to be understood that within the scope of the described invention, the invention may be practiced otherwise than as specifically described.

REFERENCES

Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251–270 (1991).

Capecchi, "Altering the genome by homologous recombination" Science, 244:1288–1292 (1989).

Cregg et al., "Recent advances in the expression of foreign genes in Pichia pastoris, "*Bio/Technology*, 11:905–910, (1993).

Davies et al., "Targeted alterations in yeast artificial chromosomes for interspecies gene transfer", *Nucleic Acids Research*, 20(11): 2693–2698 (1992).

Dickinson et al., "High frequency gene targeting using insertional vectors", *Human Molecular Genetics*, 2(8): 1299–1302 (1993).

Duff and Lincoln, "Insertion of a pathogenic mutation into a yeast artificial chromosome containing the human APP gene and expression in ES cells", *Research Advances in Alzheimer's Disease and Related Disorders*, 1995.

Gilboa, et al., "Transfer and expression of cloned genes using retroviral vectors," *BioTechniques*, 4(6):504–512, (1986).

Huxley et al., "The human HPRT gene on a yeast artificial chromosome is functional when transferred to mouse cells by cell fusion", *Genomics*, 9:742750 (1991).

Jakobovits et al., "Germ-line transmission and expression of a human-derived yeast artificial chromosome", *Nature*, 362:255–261 (1993).

Lamb et al., "Introduction and expression of the 400 kilobase precursor amyloid protein gene in transgenic mice", *Nature Genetics*, 5:22–29 (1993).

Pearson and Choi, "Expression of the human b-amyloid precursor protein gene from a yeast artificial chromosome in transgenic mice," *Proc. Natl. Acad. Sci. USA*, 90:10578–82 (1993).

Rothstein, "Targeting, disruption, replacement, and allele rescue: integrative DNA transformation in yeast" in *Methods in Enzymology*, Vol. 194, " Guide to Yeast Genetics and Molecular Biology", eds. C. Guthrie and G. Fink, Academic Press, Inc., Chap. 19, pp. 281–301 (1991).

Schedl et al., "A yeast artificial chromosome covering the tyrosinase gene confers copy number-dependent expression in transgenic mice", *Nature*, 362:258–261 (1993).

Strauss et al., "Germ line transmission of a yeast artificial chromosome spanning the murine $a_1$ (I) collagen locus", *Science*, 259:1904–1907 (1993).

We claim:

1. A method for isolating DNA comprising:
   (a) providing a leukodepletion filter device having cellular retentate containing leukocytes;
   (b) lysing the cellular retentate to form a cell lysate;
   (c) treating the filter to remove cell lysate from the filter while retaining leukocyte nuclei with the filter;
   (d) rupturing leukocyte nuclei retained with the filter in step (c) and removing contaminants while retaining the nucleic acid; and
   (e) eluting the nucleic acid from the filter.

2. The method according to claim 1, wherein the nucleic acid comprises DNA.

3. The method according to claim 2, wherein the DNA comprises genomic DNA.

4. The method according to claim 1, wherein the nucleic acid comprises genomic DNA and further comprising:
   (f) using the eluted genomic DNA for genetic analysis.

5. The method according to claim 1, wherein the cellular retentate comprises intact blood cells.

6. The method according to claim 1, wherein the leukocytes are lysed to form the cell lysate by addition of a cell lysing agent comprising a detergent.

7. The method according to claim 1, wherein the filter composition and dimensions are selected so that the nucleic acid is retained by the filter in step (d) in the absence of ionic interaction.

8. The method according to claim 1, wherein the retaining step (d) is further defined as physically retarding the movement of the nucleic acid through the filter.

9. The method according to claim 1, wherein the leukocyte nuclei retained in step (d) are ruptured by the addition of a nucleus lysing agent comprising a non-isotonic buffer capable of causing nuclei to rupture.

10. The method according to claim 9, wherein the non-isotonic buffer is a hypotonic buffer.

11. The method according to claim 1, wherein the leukocyte nuclei retained in step (d) are ruptured by the addition of a nucleus lysing agent comprising a low-salt buffer capable of causing nuclei to rupture.

12. The method according to claim 1, which is carried out without any centrifugation steps.

13. The method according to claim 1, wherein eluting step (e) further comprises heating the filter retaining the nucleic acid to an elevated temperature of 80° C. to 95° C.

14. The method according to claim 1, wherein prior to step (b), contaminating red blood cells retained with the leukodepletion filter are lysed and removed from the filter.

15. A method for utilizing leukodepletion filter devices as a source for the isolation of nucleic acid, the method comprising:
(a) providing a leukodepletion filter device having cellular retentate containing leukocytes containing nucleic acid;
(b) lysing the cellular retentate to form a cell lysate;
(c) treating the filter to remove cell lysate from the filter while retaining leukocyte nuclei with the filter;
(d) rupturing leukocyte nuclei retained with the filter in step (c) and removing contaminants while retaining the nucleic acid;
(e) heating the filter retaining the nucleic acid to an elevated temperature of 40° C. to 125° C.; and
(f) eluting the nucleic acid.

16. The method according to claim 15, wherein the cellular retentate comprises intact whole blood cells.

17. The method according to claim 15, wherein the leukocytes are lysed to form the cell lysate by addition of detergent.

18. The method according to claim 17, wherein the detergent is sodium dodecyl sulfate at a concentration of 0.01% to 1.0% weight-by-volume.

19. The method according to claim 17, wherein the detergent is sodium dodecyl sulfate at a concentration of 0.05% to 0.5% weight-by-volume.

20. The method according to claim 15, wherein the filter composition and dimensions are selected so that the nucleic acid is retained by the filter in step (d) in the absence of ionic interaction.

21. The method according to claim 15, wherein the retaining step (d) is further defined as physically retarding the movement of the nucleic acid through the filter.

22. The method according to claim 15, wherein the leukocyte nuclei retained in step (d) are ruptured by the addition of a non-isotonic buffer capable of causing nuclei to rupture.

23. The method according to claim 22, wherein the non-isotonic buffer is a hypotonic buffer.

24. The method according to claim 15, wherein the leukocyte nuclei retained in step (d) are ruptured by the addition of a nucleus lysing agent comprising a low-salt buffer capable of causing nuclei to rupture.

25. The method according to claim 15, which is carried out without any centrifugation steps.

26. The method according to claim 15, wherein the elevated temperature is in the range of 80° C. to 95° C.

27. The method according to claim 15, wherein prior to step (b), contaminating red blood cells retained with the leukodepletion filter are lysed and removed from the filter.

28. The method according to claim 15, wherein heating step (e) further comprises:
(i) heating an elution buffer to an elevated temperature of 40° C. to 125° C.; and
(ii) adding the elution buffer to the filter.

29. The method according to claim 15, wherein heating step (e) further comprises:
(i) adding an elution buffer to the filter; and
(ii) heating the filter and elution buffer to an elevated temperature of 40° C. to 125° C.

30. The method according to claim 15, wherein heating step (e) further comprises:
(i) heating an elution buffer to an elevated temperature of 40° C. to 125° C.;
(ii) adding the elution buffer to the filter; and
(iii) heating the filter and elution buffer to an elevated temperature of 40° C. to 125° C.

31. The method according to claim 15, wherein steps (e) and (f) together are repeated at least once.

32. The method according to claim 15, wherein the nucleic acid comprises DNA.

33. The method according to claim 15, wherein the nucleic acid comprises genomic DNA.

34. The method according to claim 15, wherein the nucleic acid comprises genomic DNA and further comprising:
(g) using the eluted genomic DNA for genetic analysis.

* * * * *